United States Patent [19]

Prest et al.

[11] Patent Number: 4,746,528
[45] Date of Patent: May 24, 1988

[54] GEL SYSTEM

[75] Inventors: Colin T. Prest, Stathern, Nr. Melton Mowbray; Keith Buckley, Melton Mowbray, both of England

[73] Assignee: Mars G.B. Limited, London, England

[21] Appl. No.: 903,857

[22] Filed: Aug. 29, 1986

Related U.S. Application Data

[63] Continuation of Ser. No. 808,164, Dec. 12, 1985, abandoned.

[30] Foreign Application Priority Data

Dec. 14, 1984 [GB] United Kingdom ............... 8431699

[51] Int. Cl.$^4$ ............................................. A23L 1/04
[52] U.S. Cl. .................................. 426/573; 426/805; 426/659; 426/580; 252/315.1; 435/240.1; 536/1.1; 536/114; 536/119; 424/49
[58] Field of Search ............... 426/573, 659, 580, 805; 252/315.1, 355; 435/240; 536/1

[56] References Cited

U.S. PATENT DOCUMENTS

| | | | |
|---|---|---|---|
| 4,326,052 | 4/1982 | Kang et al. | 536/1 |
| 4,326,053 | 4/1982 | Kang et al. | 536/1 |
| 4,517,216 | 5/1985 | Shim | 426/573 |
| 4,563,366 | 1/1986 | Baird | 426/573 |
| 4,647,470 | 3/1987 | Sanderson et al. | 426/573 |

FOREIGN PATENT DOCUMENTS 59-88051 5/1984 Japan .

Primary Examiner—Jeanette Hunter
Attorney, Agent, or Firm—Curtis, Morris & Safford

[57] ABSTRACT

A gellable composition comprises a mixture of (1) gellan, (2) xanthan gum, and (3) a galactomannan and/or glucomannan gum capable of producing a gel in combination with xanthan gum, especially carob, tara, cassia or konjac gum, wherein the ratio by weight range of (1):[(2)+(3)] is 1:$\geq$2.

21 Claims, No Drawings

GEL SYSTEM

This application is a continuation of application Ser. No. 808,164, filed Dec. 12, 1985, and now abandoned.

BACKGROUND OF THE INVENTION

1. Field of the Invention

This invention relates to gel systems and especially to edible gel systems that can be used, for example, in food products for human or animal consumption.

2. Prior Art

The microbial polysaccharide obtained from *Pseudomonas elodea* is commercially produced by the Kelco Corporation and marketed under the trade name Gellan.

Gellan is commercially available both in its native (fully acetylated) form and in wholly or partially deacetylated form. For the purposes of this application the expression "high acetyl gellan" is used for the fully acetylated native form and "low acetyl gellan" is used for the wholly or partially deacetylated forms.

The production of the polysaccharide in native and deacetylated form and its structure are described in U.S. Pat. Nos. 4,326,052 and 4,326,053 (Kang), the disclosure whereof is hereby incorporated by reference.

Weak but elastic aqueous gels can be produced from high acetyl gellan. Firm but brittle aqueous gels comparable to those that can be obtained from agar or carrageenan can be produced from low acetyl gellan, the lower the acetyl content the greater the strength and brittleness of the gel. Deacetylation to only slight extents, for example, 15% has significant effects on the strength and brittleness of the gel. For many applications, however, a brittle gel is undesirable and a strong elastic gel with a texture comparable to that produced from gelatin is required.

It is well known that while certain polysaccharide gums can be used to form gels others will not form gels on their own. However, certain combinations of polysaccharide gums have been found to form gels even though one or more of the gums will not form a gel on its own. A synergistic effect has been found with certain polysaccharide gums whereby adding a non-gelling gum to a gelling gum a significant increase in gel strength is obtained. Gels can also be produced from certain combinations of gums of which none of the individual gums will form gels. In this manner combinations of polysaccharide gums or polysaccharide gums with other gelling agents can produce gels with desirable textures and/or strength. Carob gum, will not gel on its own but in combination with agar or carrageenan will produce a much stronger and more elastic gel than is obtained from agar or carrageenan alone. Moreover, xanthan gum will not form a gel on its own but in combination with certain galactomannan gums such as carob, tara and cassia gums, which will also not form gels on their own, produces useful gels.

Glucomannan gums will produce thermo-irreversible gels under strongly alkaline conditions. In combination with xanthan gum, however, strong thermo-reversible gels can be produced under acid to neutral conditions.

It has been observed in the literature that combinations of gellan with small amounts of other gums such as xanthan guar or carob gum will reduce syneresis in a gel but no marked improvement in the strength or texture of the gel is observed. U.S. Pat. No. 4,517,216 (Shim), the disclosure whereof is hereby incorporated by reference, discloses that the only gelling agent that produces any synergistic improvement in gel strength when used in combination with gellan is gelatin. This patent specification discloses that many gelling agents were tested by the applicants, in combination with gellan to try to achieve a synergistic increase in gel strength, including carrageenan, carob gum, sodium alginate, corn starch and pectin. Of these only carrageenan gave a small increase in gel strength, but this was considered to be primarily because of the presence of various salts in the carrageenan affecting gelling of the gellan rather than the carrageenan itself. All of the other agents tested reduced gel strength. Moreover, the effect with gelatin was only noticed with low acetyl gellan.

SUMMARY OF THE INVENTION

This invention is based on the invention that tertiary combinations of (1) gellan, (2) xanthan gum and (3) a galactomannan and/or glucomannan gum that will form a gel in combination with xanthan gum produce very strong elastic gels.

DESCRIPTION OF PREFERRED EMBODIMENTS

The galactomannan gum is preferably carob gum, tara gum or cassia gum, although any other galactomannan gum that in combination with xanthan gum will produce a gel that may be used. The glucomannan gums that can be used are preferably those that are present in various Amorphophallus species, and especially A. Rivieri and its varieties, often referred to as *A. Konjac, A. Oncophyllus, A. Variabilis, A. Bulbifera* and *A. Blumeii.* The preferred glucomannan from an Amorphophallus species is konjac gum which is present in, for example *A. Konjac.*

The gellan used according to the invention may be either high or low acetyl gellan but is preferably a low acetyl gellan, either wholly or partially deacetylated. Partially deacetylated gellan preferably has at least 20%, and more preferably at least 50% of the acetyl groups removed.

Preferably, the total amount of gums in the gel is from 0.1–5% by weight based on the weight of the aqueous phase and preferably the ratios of gellan:xanthan gum; galactomannan or glucomannan gum:xanthan; and gellan:galactomannan or glucomannan gum each lie within the range of from 5:1 to 1:5. Particularly good gels have been found to be formed at a ratio of gellan:xanthan gum:carob or cassia or konjac gum of within the range of 1:1 to 2:1 to 2 and especially approximately 1:1.5:1.5. When tara gum is used a somewhat higher proportion is desirable and the preferred ratio of gums is 1:1.5:2 to 3.

The gels can be produced in both the alkaline and acid range. Preferably for use in foodstuffs the gels are produced in the neutral to acid range (pH 3 to 8). If the gel is to be produced in a heat sterilised product, it is desirable to maintain the pH of the gel above about 6, especially when a galactomannan is present because at more acid pH some of the galactomannan gums tend to breakdown on heating. If the gel is to be used in a product which is not going to be subjected to high temperature sterilisation the pH may extend well into the acid range, for example, down to about pH 3.

The gallan and other gums may be used in purified or natural form depending on the intended application of the gel. By "natural" form of the gum is meant the gum mixed with all or a part of the material in which it is produced or occurs. Thus, for example, natural carob gum consists of the comminuted endosperm of the carob bean, possibly with some associated residual husk of the bean. The purified form of the gum is the gum separated from at least the greater part of that material. In those cases where transparency is important, the purified form of the gum is preferably used but for other applications where the opacity introduced by the presence of impurities can be tolerated, the impure forms of the gums can be used.

The gelling systems of the invention have particular application in human and animal foods, such as confectionery, water- or milk-based fruit gels and other deserts, pie fillings, pet foods, icings and frostings and dairy products, and especially in pasteurised or sterilised food products, but can also be used for many other applications where a strong elastic gel is required such as air freshners, tooth paste and tissue culture media.

The following examples illustrate the invention. In the examples the abbreviation L.A. means low acetyl and H.A. means high acetyl. The low acetyl gellan used in the examples is substantially acetyl free. The high acetyl gellan as indicated hereinbefore is the native gum. The carob, tara, cassia and konjac gums used were the natural forms of these gums, comprising approximately 50% gluco- or galacto-mannan combined with extraneous vegetable matter remaining from their source material.

EXAMPLE 1

Various combinations of gums as indicated in Table 1, were dispersed in a mixed phosphate buffer system of pH 6.6 at room temperature and the dispersion was boiled for 15 minutes to disolve the gums. The solution was then transferred to 75×215 mm cans and sealed hot to exclude air. The cans were then sterilised in a steam autoclave at 127° C. for 59 minutes. The solutions were poured into petri dishes while still hot and allowed to cool-overnight before being tested for breakstrength and elasticity using an Instron (Registered Trade Mark) Food Tester 1140 fitted with a 27 mm dia plunger.

TABLE 1

| Gums | Conc' (%) | Breakstrength (g) | Elasticity (mm) |
|---|---|---|---|
| L.A. Gellan | 0.3 | 161 | 4.9 |
| L.A. Gellan | 0.3 | 169 | 5.7 |
| Carob | 0.45 | | |
| L.A. Gellan | 0.3 | | |

TABLE 1-continued

| Gums | Conc' (%) | Breakstrength (g) | Elasticity (mm) |
|---|---|---|---|
| Xanthan | 0.45 | 132 | 6.9 |
| Carob | 0.45 | 784 | 8.7 |
| Xanthan | 0.45 | | |
| L.A. Gellan | 0.3 | | |
| Carob | 0.45 | 1248 | 7.3 |
| Xanthan | 0.45 | | |
| H.A. Gellan | 0.3 | 47.2 | 5.99 |
| H.A. Gellan | 0.3 | | |
| Carob | 0.45 | 818 | 7.62 |
| Xanthan | 0.45 | | |
| L.A. Gellan | 0.3 | | |
| Xanthan | 0.45 | 1181 | 6.85 |
| Cassia | 0.45 | | |
| L.A. Gellan | 0.3 | | |
| Xanthan | 0.45 | 1106 | 6.95 |
| Tara | 1.1 | | |

EXAMPLE 2

Gums were dispersed and processed in a mixed phosphate buffer system at pH 6.1 as described in Example 1. The results are shown in Table 2.

TABLE 2

| Gums | Conc' (%) | Breakstrength (g) | Elasticity (mm) |
|---|---|---|---|
| Konjac | 0.45 | 253 | 9.5 |
| Xanthan | 0.45 | | |
| L.A. Gellan | 0.3 | 120 | 5.5 |
| Konjac | 0.45 | | |
| L.A. Gellan | 0.3 | | |
| Konjac | 0.45 | 559 | 7.2 |
| Xanthan | 0.45 | | |

EXAMPLE 3

Pet food products were prepared in cans, the recipe containing approximately 50% meats and 50% gravy. The meats were made up of a mixture of lungs, tripe and various offals, trims and muscle meats. The gravy contained gums, dyes, salts and water. The products were sterilised in a steam heated autoclave at 129° C. for 59 mins. After cooling the cans were opened and a subjective assessment of the external gel quality and meat pack strength was made.

TABLE 3

| Gums | Conc % | Gel Qualities | Pack Qualities |
|---|---|---|---|
| L.A. Gellan | 0.2 | Very weak, soft, brittle | Soft, easily broken up |
| L.A. Gellan | 0.3 | Fairly firm, very brittle | Firm, brittle |
| L.A. Gellan | 0.4 | Firm, very brittle | Solid, firm |
| Carob | 0.3 | Hardly any evident gel | Just self supporting moussey/blancmange-like appearance |
| Xanthan | 0.3 | Soft mucus like | |
| Carob | 0.3 | | |
| Xanthan | 0.3 | Fairly firm, elastic | Fairly firm, elastic |
| L.A. Gellan | 0.2 | | |
| Carob | 0.3 | | |
| Xanthan | 0.3 | Fairly firm, elastic | Very firm, rather brittle |
| L.A. Gellan | 0.4 | | |
| Xanthan | 0.4 | Very soft, elastic mucus like | Very moussey, soft integral elastic |
| Konjac | 0.4 | | |
| Xanthan | 0.3 | | |
| Konjac | 0.3 | Soft, elastic | Slightly soft, elastic |
| L.A. Gellan | 0.2 | | |
| Xanthan | 0.4 | Slightly soft, fairly elastic | Fairly firm, elastic |
| Konjac | 0.4 | | |
| L.A. Gellan | 0.4 | | |

TABLE 3-continued

| Gums | Conc % | Gel Qualities | Pack Qualities |
|---|---|---|---|
| Tara | 0.7 | | |
| Xanthan | 0.3 | Fairly firm, elastic | Fairly firm, elastic |
| L.A. Gellan | 0.2 | | |
| Cassia | 0.3 | | |
| Xanthan | 0.3 | Fairly firm, elastic | Fairly firm, elastic |
| L.A. Gellan | 0.2 | | |

EXAMPLE 4

A fruit dessert was prepared using the following formulation at a pH of 4 to 4.5:

| | |
|---|---|
| Water | 85.61% |
| Sugar | 13.00% |
| Citric Acid | 0.85% |
| L.A.Gellan | 0.12% |
| Xanthan | 0.18% |
| Carob | 0.18% |
| Orange Flavour | 0.05% |
| Colouring | |
| F D and C Yellow No. 6 | 0.0096% |
| F D and C Red No. 2 | 0.0004% |

The gel was firm and elastic and had a satisfactory texture as a jelly fruit dessert comparable with that produced using conventional gelling agents.

We claim:

1. A gellable composition adaptable to the formation of an unsterilized gel having superior gel strength, said composition comprising a mixture of (1) gellan, (2) xanthan gum, and (3) a galactomannan and/or glucomannan gum capable of forming a gel with xanthan gum, wherein the ratio by weight of (1):[(2)+(3)] is $1:\geqq 2$.

2. A composition according to claim 1, incorporating a glucomannan gum and, wherein the glucomannan gum is a glucomannan derived from an Amorphophallus species.

3. A composition according to claim 2, wherein the glucomannan gum is konjac gum.

4. A composition according to claim 1, incorporating a galactomannan gum and wherein the galactomannan gum is carob gum, tara gum or cassia gum.

5. A composition according to claim 1, wherein the gellan is a low acetyl gellan.

6. A composition according to claim 1, wherein the ratio of gellan:xanthan; gellan:galactomannan or glucomannan; and xanthan:galactomannan or glucomannan each lie within the range of from 5:1 to 1:5.

7. A composition according to claim 6, comprising gellan, xanthan gum and carob, cassia or konjac gum in a ratio within the range of 1:1 to 2:1 to 2.

8. A composition according to claim 7, comprising gellan, xanthan gum and carob, cassia or konjac gum in a ratio of substantially 1:1.5:1.5.

9. A composition according to claim 6, comprising gellan, xanthan gum and tara gum in a ratio within the range of 1:1 to 2:2 to 3.

10. A composition according to claim 1, wherein the gellan and other gums are present in the composition in natural form.

11. A gellable composition adaptable to the formation of a sterilized gel having superior gel strength, said composition comprising a mixture of (1) gellan, (2) xanthan gum, and (3) a galactomannan and/or glucomannan gum capable of forming a gel with xanthan gum, wherein the ratio by weight of (1):[(2)+(3)] is $1:\geqq 1.5$.

12. A composition as in claim 11 comprising a glucomannan gum derived from an Amorphophallus species.

13. A composition as in claim 11 comprising a glucomannan gum which is konjac gum.

14. A composition as in claim 11 comprising a galactomannan gum which is carob gum, tara gum, or cassia gum.

15. A composition as in claim 11 wherein the gellan is a low acetyl gellan.

16. A composition as in claim 11 wherein the ratios of gellan:xanthan; gellan:galactomannan or glucomannan; and xanthan:galactomannan or glucomannan each lie within the range from 5:1 to 1:5.

17. A composition as in claim 16 comprising (1) gellan, (2) xanthan gum, and (3) carob, cassia, or konjac gum in a ratio within the range 1:1 to 2:1 to 2.

18. A composition as in claim 17 comprising (1) gellan, (2) xanthan gum, and (3) carob, cassia, or konjac gum in a ratio of about 1:1.5:1.5.

19. A composition as in claim 16 comprising (1) gellan, (2) xanthan gum, and (3) tara gum in a ratio within the range 1:1 to 2:2 to 3.

20. A composition as in claim 11 wherein the gellan and other gums are present in the composition in natural form.

21. An aqueous gellable system comprising an aqueous phase and a composition as in claim 11 in a total amount from 0.1 to 5 percent by weight of the aqueous phase.

* * * * *